United States Patent [19]

Piran et al.

[11] Patent Number: 6,087,088
[45] Date of Patent: *Jul. 11, 2000

[54] BINDING ASSAYS USING MORE THAN ONE LABEL FOR DETERMINING ANALYTE IN THE PRESENCE OF INTERFERING FACTORS

[75] Inventors: Uri Piran, Sharon; John J. Quinn, Medway, both of Mass.

[73] Assignee: Bayer Corporation, East Walpole, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/791,591

[22] Filed: Jan. 31, 1997

[51] Int. Cl.[7] ........................................... C12Q 1/00
[52] U.S. Cl. ................................. 435/4; 435/7.9
[58] Field of Search ............................. 435/4, 7.92, 7.94, 435/7.93, 7.9, 962; 436/518, 538, 540

[56] References Cited

U.S. PATENT DOCUMENTS

| | | | |
|---|---|---|---|
| 4,713,347 | 12/1987 | Mitchell et al. | 436/501 |
| 5,278,080 | 1/1994 | Midgley et al. | 436/500 |
| 5,366,859 | 11/1994 | Miyoshi et al. | 435/5 |
| 5,380,649 | 1/1995 | Berry et al. | 435/22 |
| 5,384,246 | 1/1995 | Berry et al. | 435/22 |
| 5,384,247 | 1/1995 | Berry et al. | 435/22 |
| 5,409,814 | 4/1995 | Berry et al. | 435/22 |
| 5,614,367 | 3/1997 | Kaluza et al. | 435/7.1 |

FOREIGN PATENT DOCUMENTS

| | | |
|---|---|---|
| 2169121 | 8/1996 | Canada . |
| 0536593 | 4/1993 | European Pat. Off. . |
| 0726464 | 8/1996 | European Pat. Off. . |
| 87/07955 | 12/1987 | WIPO . |
| 94/03811 | 2/1994 | WIPO . |
| 97/01763 | 1/1997 | WIPO . |
| 97/41442 | 11/1997 | WIPO . |

OTHER PUBLICATIONS

Blake C. Simultaneous Enzyme Immunoassay of Two Thyroid Hormones. Clinical Chemistry 28(7) 1469–1473, 1982.
Comeau et al., "An Automated Chemiluminescent Immunoassay Test For Total Triiodothyronine," 43rd National Meeting of the American Association for Clinical Chemistry, Inc., Washington, D.C., USA, Jul. 28–Aug. 1, 1991. Clin Chem 37 (6). 1991. 941.

*Primary Examiner*—Ralph Gitomer
*Attorney, Agent, or Firm*—Arthur S. Morgenstern

[57] ABSTRACT

Novel binding assay techniques have been developed which improve accuracy and sensitivity via accounting for interfering factors. They rely on use, in a simultaneous incubation, of two or more different labels, some of which are used primarily to detect analyte, and others to detect interfering substances originating in the sample. The mathematical relationships between the labels allow corrections that lead to more accurate and sensitive determination of the presence and concentration of the analyte.

24 Claims, 5 Drawing Sheets

BINDING ASSAYS USING MORE THAN ONE LABEL FOR DETERMINING ANALYTE IN THE PRESENCE OF INTERFERING FACTORS

BACKGROUND

In developing a binding assay, it is important that the scientist develop one that has a high level of sensitivity, precision and specificity, can eliminate interfering substances, and is convenient. The discussion herein may emphasize the immunochemical-type assay, but it should be recognized that the descriptions are also applicable to gene probe and other types of binding assays.

Sensitivity means the minimal detectable dose, namely the smallest mass of analyte that generates a statistically significant change in the signal generated by the assay vs. that obtained in the absence of analyte. There is a need to increase sensitivity of binding assays (i.e., detect smaller amounts of analyte), because in many situations the analytes, whether they are hormones, drugs, microorganisms, toxins, pollutants or genetic materials, exert their effects at low concentrations.

Furthermore, high sensitivity allows the use of small sample size, which can help to reduce "sample matrix" interferences. In addition, higher sensitivity allows measuring low analyte concentrations with a higher precision.

In discussing sensitivity, immunochemists have often distinguished between competitive assays and non-competitive assays. In a competitive assay, the signal which is measured is that emanating from the specific binder that does not bind analyte. For example, in some competitive assays, the labeled antibody is incubated with a sample containing analyte and a solid phase-immobilized analyte derivative. The labeled antibody that did not bind analyte binds the solid phase, and the signal emanating from the solid phase-bound labeled antibody is measured. In other types of competitive assays, unlabeled antibody is incubated with a sample containing an analyte and a labeled analyte derivative (or analyte mimic). The labeled analyte derivative binds those antibody binding sites that did not bind analyte. By measuring the signal coming from the labeled analyte derivative that bound the antibody, the assays actually obtains an estimate of the concentration of antibody sites that did not bind analyte. Thus, in both types of competitive assays, one measures signal associated with the fraction of specific binder sites that did not bind analyte. The signal generated from a competitive assay decreases as the analyte concentration increases. Since small levels of analyte correspond to large signals, small changes in low concentrations of analyte lead to small differences between large numbers, which are hard to measure accurately.

A second type of binding assay is the non-competitive type. In this assay, a labeled specific binder, for example a labeled antibody, is incubated with the sample and binds a portion of the analyte. In one variation (type A) of noncompetitive assay, a solid-phase immobilized unlabeled specific binder is added, simultaneously or in sequence, to bind another epitope on the analyte, in which case it is called a "sandwich" assay. For example, the immobilized molecule might be an antibody against a second epitope on the analyte, and the analyte might form a ternary complex with the labeled antibody and an immobilized unlabeled antibody. The solid phase is then washed and the signal measured is the signal that comes from the ternary complex containing the analyte. In this case the signal increases with increasing analyte concentration. Another variation of the non-competitive immunoassay (type B) was invented by L. E. M. Miles and C. N. Hales, Nature 219:186, 1968. In this type of assay the labeled antibody is first incubated with the analyte to form an immune complex, and then the mixture is contacted with a solid phase. This solid phase has an analyte derivative (or mimic) in large excess, which causes the unreacted labeled antibody to bind to it. The solid phase is then separated from the liquid phase and a portion of the liquid phase is taken for signal measurement. The difference from the competitive type of assay is that one does not measure the signal associated with the solid phase, namely the labeled binder that did not bind analyte. What one measures, instead, is the signal associated with the labeled binder that bound analyte and consequently did not bind the immobilized binder, thus remaining in the liquid phase. Improved versions of the non-competitive type B immunoassay include those invented by Baier et al. U.S Pat. No. 4,670,383, 1987 and Piran et al. U.S. Pat. No. 5,445,936, 1995.

Type A of the non-competitive assay has the potential for the highest sensitivity. Jackson and Ekins (T. M. Jackson and Ekins, R. P., Journal of Immunological Methods, 87:13, 1986) showed by mathematical analysis that when the specific activity of the label is not limiting, the sensitivity of type A is higher than that of the competitive assay. Empirical data supports the conclusion that type A of immunoassays is more sensitive than the competitive type of immunoassays: several immunoassays, such as thyroid stimulating hormone, have sensitivity of several million molecules per assay cuvette; in contrast, the most sensitive competitive immunoassays, such as those of digoxin and triiodothyronine, have sensitivities of several billion molecules per assay cuvette. There is a need to improve the sensitivities of non-competitive assays even further, and one way of achieving this improvement is via reduction of "nonspecific binding" (NSB), namely, the nonspecific adsorption of the labeled specific binder to the solid phase and the reaction vessel. Another way of increasing sensitivity according to Jackson and Ekins is to reduce the variability of the non-specific binding (NSB).

Interfering Factors

Often the sample to be analyzed in an immunoassay is delivered in an environment that includes interfering factors. For example, a serum sample not only contains the analyte of interest, but also many components that could interfere with the immunoassay. These interfering factor include not only well-defined and predictable molecules, present in higher-than-normal concentrations. However, they also can include materials which are not well-defined. Some immunochemical assay techniques include steps that isolate the analyte from the interfering substances. For example, the analyte can be reacted with an antibody which is connected to a solid phase. The solid phase can then be separated from the other components in its environment and incubated with a labeled specific binder, thus minimizing the contact of interfering factors with the labeled specific binder. However, the separation step in immunoassays is more often designed to only separate the bound portion of the labeled specific binder from the unbound portion. Although a small amount of the interferring substances may be eliminated via the traditional separation step, other means for eliminating the balance of the interferences from sample matrix are needed.

The separation step referred to above can be accomplished in one of many ways. For example: an assays can use non-magnetic particles as the solid phase using either centrifugation filtration as the method of separation, or magnetic particles as the solid phase, in which case the separation is accomplished by the application of a magnetic field. Other effective means of separation involve various chromatographies, electrophoreses, and the use of extended surfaces, such as microtiter plates, large beads, fibers and others. The separation step can be done manually or by an automated or non-automated instrument; in either case, however, the solid phase is separated and washed, the liquid phases are discarded, and the solid phase-associated signal is the one being measured.

Many substances interfere with the assays despite the wash steps. For example, cross-reactants share structural similarities with the analyte and also bind the labeled or unlabeled specific binder. When a cross-reactant binds the labeled specific binder the assay result is falsely elevated. When sufficiently high concentration of a cross-reactant binds the unlabeled specific binder and saturates it, a false result is obtained.

Occasionally the analyte itself is present in an extremely high concentration, causing an interference in two-site (sandwich) noncompetitive assays known as "high dose hook effect." This interference manifests itself as a falsely low signal, which makes a very high dose to be confused with a low dose. Other interfering factors are heterophilic antibodies, human anti-mouse IgG antibodies, human antibodies to gamma globulin of other animal species, rheumatoid factors and other macromolecules present in the sample can bind antibodies and can either form a bridge between the labeled and unlabeled antibodies or inhibit their desired binding activity, leading in each case to false results. Similar interfering factors are present in other binding assays, such as gene probe assays. The effect of these interferences is usually to provide inaccurate result; however, in the low analyte concentration region interfering factors can increase the variability of the "zero dose signal" and thus reduce sensitivity. Therefore, correction for interfering factors can increase sensitivity of the assay.

SUMMARY OF THE INVENTION

Novel non-competitive binding assay techniques have been developed which account for the effects of interfering factors, thereby providing higher accuracy and sensitivity. They rely on use of two or more different labels. The first label is used primarily to detect analyte, and the other labels are reference labels used to detect and quantitate the effect of interfering factors originating in the sample.

The incubation and readout of the labels can be carried out simultaneously, and the mathematical relationship between the signals of first label and the reference label(s) allows detection of the interference and a mathematical correction of the result.

DETAILED DESCRIPTION OF THE INVENTION

Binding assay techniques that account for interfering substances in an assay, and are therefore more accurate and sensitive, are described herein. One of its primary applications is in the field of immunochemistry; and thus, most of the discussion of the techniques is related to the immunochemistry field. However, it should be noted that the techniques are equally applicable to other binding assays, such as gene probe assays, which involve hybridization of complementary nucleic acids via base pairing, and receptor assays. These binding assay techniques are suitable for a wide diversity of analytes, including those with one or more epitopes. Analytes may include proteins, peptides, drugs, hormones, receptors, antibodies, microorganisms, environmental pollutants, nucleic acids, lipids, surfactants, carbohydrates and various conjugates of these. This also can include binding assays for whole cells and cell fragments. These techniques are suitable for both determination of the total amount of analyte in the sample or the free fraction (e.g. free hormones and free drugs in biological fluids).

A typical application of the invention to immunoassay procedures is as follows: to the analyte of interest are added two labeled antibodies. The first is an antibody to the analyte, and the second is preferably an antibody specific to the binding site on the unlabled specific binder (antibody or antigen) that is usually immobilized on a solid phase, or a nonspecific IgG from an organism of the same species as the first antibody or otherwise is as structurally similar to the first antibody as possible (e.g. same isotype), but which is an antibody to an epitope that does not occur on the analyte of interest.

Preferably, the second labeled antibody does not recognize any material present in the sample when interfering factors are not present in the sample. The second antibody that is used to measure interference is also called herein a reference antibody, and a more general term encompassing other labeled such reagents is defined herein as a reference binder. Each of these labeled antibodies should be attached to a different label, so that the signal emanating from each antibody can be distinguished from that emanating from the other. The signal emanating from the second antibody, which is the reference antibody, is a measure of the interference, and the amount of signal emanating from the reacted second antibody should be used to either alert the analyst of an interference (i.e., serve as a qualitative indication of the presence of an interference) or be used to mathematically correct the signal of the first antibody (i.e., quantitative), in order to obtain a more precise indicator of the amount of analyte present. Thus, when the signal emanating from the reference binder is statistically different from the signal in the absence of interfering factors, there is an indication that an interfering factor is present, and the analyte concentration measured by the first label is not valid. A further improvement is a mathematical correction of the result, such that the corrected result is rendered valid.

The mathematical correction is preferably done by a simple linear or quadratic model, such as ratio or difference, based on empirical experiments with serum spiked by interfering factors, but can be done in some cases by a more complicated mathematical relationship between the labels, such as a cubic model. Application of the invention to nucleic acid hybridization assays involves a target (analyte)-specific probe labeled with first label and an interference-detecting probe (reference probe) with a second label attached to it. The second labeled probe is preferrably specific to an immobilized unlabeled probe. Alternatively, it may be a probe with no complementarity to the target that binds interfering factors due to physical-chemical properties common to gene probes in general.

Similarly, binding assays to other types of analytes can be constructed with two labels: one for direct binding to the analyte and the other for detecting and quantitating the interference. To detect additional interferences it is possible to use more than one reference binder, preferrably with all of the reference binders being labeled with the same second label.

Figure 1:
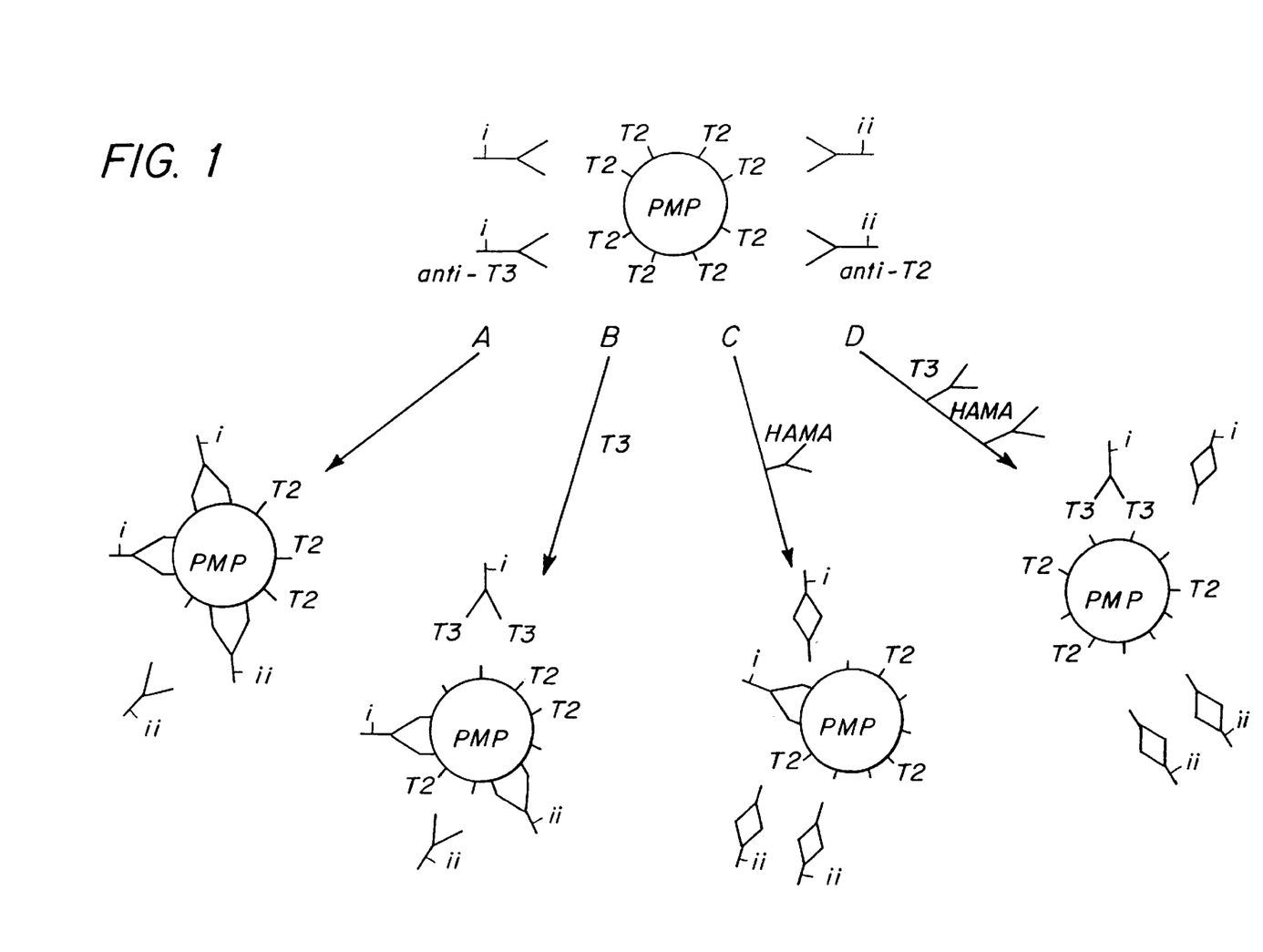
FIG. 1. depicts a scheme for a triiodothyronine (T3) competitive immunoassay with a first label (i) attached to a mouse monoclonal anti-T3 and a second label (ii) attached to the reference binder mouse monoclonal anti-diiodothyronine (T2), using paramagnetic particles (PMP) as the solid phase, having immobilized T2.

An example of a competitive immunoassay for triiodothyronine (T3) is depicted in FIG. 1. The figure shows how the presence of human anti mouse antibody (HAMA) interfers with the normal functioning of the assay, but is detected by label ii. The anti-T3 is labeled with label i, and the reference antibody is anti-diiodothyronine (T2) labeled by label ii. The solid phase is coupled to T2. In reaction A the sample does not contain either T3 or interference factor, thus both labels bind the solid phase-immobilized T2. In reaction B the sample contains T3; therefore, i-labeled anti-T3 binding to the solid phase is reduced and the binding of ii-labeled anti-T2 remains same as in reaction A. In reaction C the sample contains the interfering factor human anti-mouse IgG, which reduces the binding of both labels i and ii to the solid phase. In reaction D both T3 and an intereefering factor heterophilic antibody, or human anti-mouse IgG antibody, are present in the sample;therefore, binding of both labels is reduced, with I being reduced more than in reaction C. An interferring factor in the sample, e.g. human anti-mouse IgG, will bind to anti-T3 and inhibit its binding to the solid phase-immobilized T2, causing a falsely elevated T3. The presence of anti-T2 in the reaction does not interfere with the assay because the amount of anti-T2 is set at a very low level and is constant in each assay reaction. Some interferring factors may increase the binding of anti-T3 to the solid phase by bridging the anti-T3 to the solid phase; this, however, will also be detected because anti-T2 will also display an increase in solid phase binding.

Figure 2:
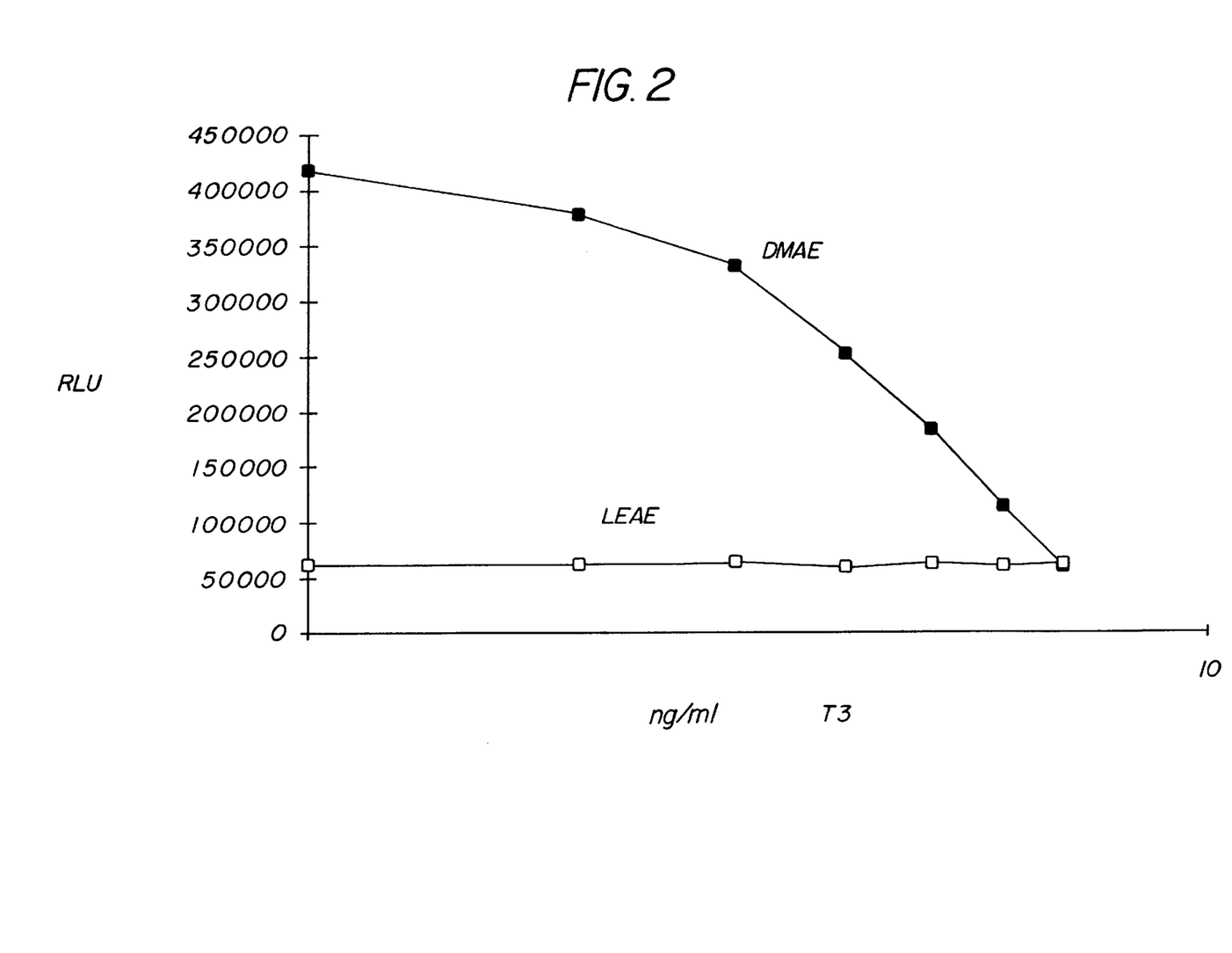
FIG. 2. shows a calibration curve of a T3 immunoassay obtained as described in Example 1, using DMAE-labeled anti-T3 and LEAE-labeled T2 as the labels.

When a significant change in the signal of the reference label is detected, it is qualitatively apparent that the sample result should be held in suspect. In order to exploit the information quantitatively, it is necessary to calibrate the assay not only in a two dimensional curve, as shown in FIG. 2, but also three dimensionally; for example, the RLU vs. T3 calibration should be done in the presence of several concentrations of anti-mouse IgG. This three-dimensional calibration will allow the user to obtain a corrected T3 conscentration in the sample despite the presence of the interference. One reference labeled binder is generally sufficient for competitive binding assays, because NSB and high-dose-hook effects are not relevant to this type of assays, and the preferred reference binder is a specific binder analogous to that described in the example for the T3 assay.

The anti-mouse IgG used for calibration purposes, as discussed above, could either be from humans or from another species. The anti-mouse IgG, by its nature, is variable in content, which poses somewhat of a problem if quantitative studies are being undertaken. To deal with the variability, calibrations should be conducted using anti-mouse IgG from several sources, which should then be validated using human samples. Immunochemists are familiar with the technique of using IgG's from various species. (I.e., this is comparable to dealing with the variability found in polyclonal antibodies.)

Figure 3:
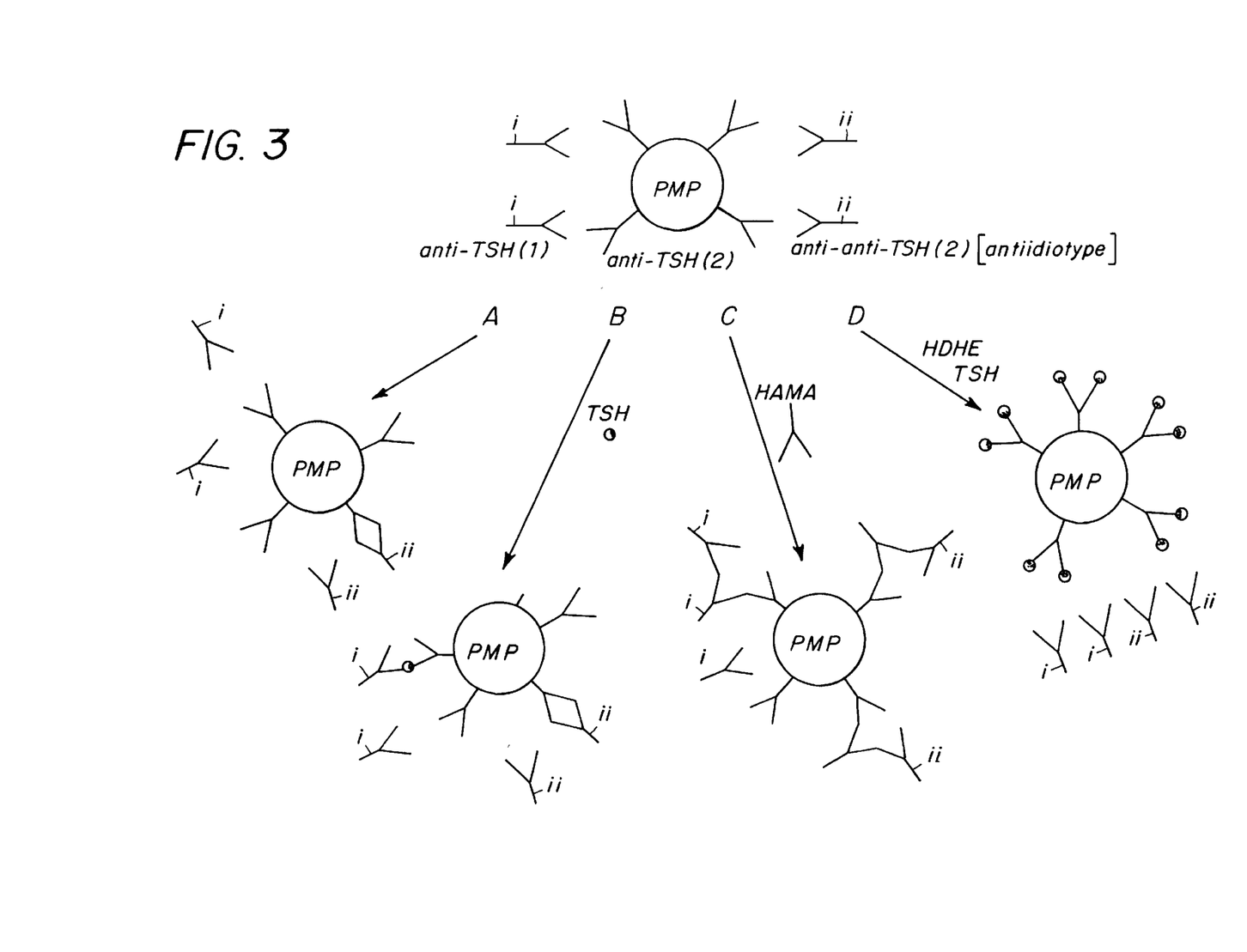
FIG. 3. depicts a scheme for a two-site non-competitive immunoassay of thyroid stimulating hormone (TSH), using DMAE-labeled anti-TSH (i-anti-TSH (1)) and another anti-TSH (2) immobilized on a solid phase. A antiidiotype anti-anti-TSH(2) is labeled by label ii, which is in this case LEAE.

An example for the application of the method in a non-competitive (sandwich) immunoassay of thyroid stimulating hormone (TSH) is depicted in FIG. 3. In FIG. 3 reaction A represents the case of zero calibrator, reaction B that of low and high calibrators or samples, reaction C represents an interference by human anti-mouse IgG antibody (HAMA), and reaction D represents the case of a "high dose hook effect." The solid phase is coupled to anti-TSH (2), and label i is attached to a different anti-TSH (1), which is directed against another epitope on TSH. Label ii is attached to an antiidiotype that is an antibody directed against the TSH binding site of the immobilized anti-TSH. In the absence of interferring factors, (reactions A and B) label i will bind to the solid phase only via the bridging effect of the analyte TSH. Label ii will bind to the solid phase only by binding directly to the immobilized anti-TSH (2), and this binding will be independent of anlalyte concentration. Interferring factors (reactions C and D) that elevate the binding of label i (anti-TSH( 1)) by a bridging mechanism will also elevate the binding of label ii, and therefore will be detected. An interferring factor that inhibit the binding of label i will also inhibit the binding of label ii. The presence of a very high TSH concentration in the sample will cause a "high dose hook effect" by saturating the immobilized anti-TSH (2), thus inhibiting binding of the complex comprising TSH and i-labeled anti-TSH (1) to the immobilized anti-TSH (2); however, this will be detected by the fact that binding of label ii to the solid phase will also be inhibited. The method can also be applied in the case of non-competitive assays involving one epitope, such as those described in U.S. Pat. No. 5,445,936, by, for example, using two different solid phases and labeled antiidiotype or anti-analyte mimic or both. In order to allow for quantitative correction of the TSH value in a high-dose-hook effect sample, calibration of RLU vs. TSH should be done using concentrations of TSH that span the range which includes the very high levels. In addition, in order to quantitate correctly in the presence of interferences such as HAMA, a three dimensional calibration ( TSH vs. RLU calibration is repeated with calibrators spiked with various amounts of HAMA) is necessary. It should be noted that a labeled reference specific binder such as the antiidiotype described above is not effective in improving sensitivity, because the signal generated by such a binder is relatively high. In order to correct for small variations of the NSB and thereby improve sensitivity, it is necessary to employ a nonspecific binder that is physically as similar as possible to the labeled specific binder (anti-TSH). Calibration of the signals emanating from the two labeled binders vs. analyte concentration (two dimensional calibration) is sufficient, but several samples devoid of analyte should be used in order to establish the correlation between the NSB of the reference label and the specific label. In addition, the use of two reference labels can allow improving both sensitivity and correction in case of high-dose-hook effect and HAMA, provided that the two reference labels are distinguishable from each other and from the labeled anti-analyte.

This technique should be distinguished from the method described by Hemmila et al. in Clin Chem vol. 12, p. 2281–2283 (1987) or U.S. Pat. No. 5,395,752 (Law et al.), because they are methods for simultaneous assay of two or more analytes, which do not utilize a reference label and do not help in addressing the interference problems. The present invention is also distinct from the technique in EP 251,707 (Hansen), since the procedure therein is designed to correct only for analyte-independent signal variations due to manufacturing defects in the solid phase or the reaction vessel.

Solid phase materials may include: paramagnetic particles (including those made as a composite of magnetic material and polymer, such as magnetic latex, or combined with other materials), particles made of controlled-pore glass, polymer particles, latex, colloidal metal or metal oxide particles, immiscible liquid phase, extended surface, porous paper, porous gel, cellulose beads, cross-linked dextran or any other particle. Particle size can vary from 10 nm to several microns in diameter, larger beads of any size, flat surfaces, testube wall, dipstick surface, fibers, membranes, porous media, rods and discs, or any extended or particulate surface capable of carrying an immobilized binder. Preferably, the solid phase material is either a paramagnetic particle or an extended surface.

Various techniques can be used for separation of the solid phase from the liquid phase, including centrifugation, filtration, settling by gravity, magnetic attraction, electrophoresis, various column chromatographies, capillary forces, etc. The present invention is also compatible with the sensor format, which does not requires removal of the liquid phase, since the sensor can read the signal that is situated near the sensor surface, with only small amount of liquid phase signal being read by the sensor. Also compatible are both batch systems, such as those used in automated laboratory instruments, and continuous flow systems. Assay formats involved in "near patient testing", such as dipsticks, immunochromatography and immunoconcentration devices are also compatible with the present invention.

The two labels can be two chemiluminescent or bioluminescent labels that have two different emmission wavelengths, two fluorescent labels with different emmission or excitation wavelengths, two different enzymes, radioactive materials, liposomes, latex particles, or a pair of any other type of labels used in binding assays. A combination of two different labels e.g. one chemiluminescent and one fluorescent or radioactive, as well as a combination of more than two labels, may be used. Examples of chemiluminescent labels include acridinium esters and their derivatives, such as dimethyl acridinium ester (DMAE) and long-emission acridinium esters (LEAE).

These novel procedures can be utilized with analytes having one epitope as well as analytes with two or more epitopes, and examples demonstrating variations in the scheme are shown below. In addition, this analytical technique can be used for procedures aside from immunoassays, such as gene probe and receptor assays. The technique is applicable to procedures using one or more than one container. Further variations are also possible, namely the use of more than 2 labels, so long as the labels can be distinguished from each other. In the case of more than 2 labels being used, several of the mathematical relationships between signals emanating from reference binders and analyte binders (e.g. ratio) can be analyzed in order to have a better estimate of amount of analyte. For example, two antibodies that react to two different interfering substances can be included in the assay. Thus, by comparing two different ratios calculated to two different calibration curves, two estimates of the concentration of analyte can be determined. Alternatively, one antibody to interfering substance can be included in an assay with antibodies to 2 different analytes. In this latter assay, one sample can be used to determine the presence of both analytes, with each analyte being determined by comparing the ratio of interference to analyte for that analyte with the calibration curve for interference:analyte ratios.

Most of the discussion above dealt with the use of two labels. If more than two labels are used, a similar extrapolation to the multi-label system should be used. For example, in a three-label system, the anti-analyte is labeled with one label (label 1), while the other two labels (label 2 and label 3) are on antibodies that bind to two interferring substances (substance 2 and substance 3) (or two groups of interferring substances, each bound by either the second or third labeled substance). The ratio of label 2 to label 1 is used to account for one interference caused by substance 2, while an analogous ratio is used to account for substance 3.

The following examples illustrate the procedure of this invention but are not intended to limit its usefulness.

EXAMPLES:

Example 1

Competitive immunoassay for triiodothyronine (T3).

Monoclonal anti-T2 was prepared by immunizing Balb/c x A/J F1 mice three times with about 0.1 mg T2-BGG. Spleen cells were fused to SP2/0 myeloma cells using conventional techniques. Hybridoma supernatants were tested for binding to DMAE-T2-BGG in the presence of 0.5% BGG, to block anti-BGG antibodies. Cross-reactivity to T3 and T4 was determined by competitive immunoassay. Cell lines were cloned by limiting dilution method and ascitic fluid was produced in pristane primed CAF1 mice.

Monoclonal anti-T3 antibody and BGG-T2 were prepared as previously described by Piran et al. in Example 1, U.S. Pat. No. 5,445,936. BGG-T2 was immobilized on PMP by the glutaraldehyde method of Groman et al., Bio Techniques, vol. 3, pp. 156–160 (1985). Anti-T3 was labeled with dimethyl acridinium ester (DMAE), and anti-T2 was labeled with long emission acridinium ester (LEAE) (See U.S. Pat. No. 5,395,752), essentially as described by Law et al. in J. Biolumin. Chemilumin. Vol. 4, pp. 88–98 (1989).

For the T3 assay 0.05 ml calibrators were mixed with 0.1 ml releasing agent (0.2 M NaOH) in polystyrene tubes and incubated for 15 min. The solid phase PMP-BGG-T2, 5 $\mu$g, was added in 0.25 ml of Buffer A containing, per liter, 140 mmole sodium phosphate, 20 mmole sodium barbital, 4 mmole sodium chloride, 1 mmole ethylenediaminetetraacetic acid (EDTA), 0.15 g 8-anilino-naphtalenesulfonic acid, 1 g sodium azide, 0.02 g BGG and 2.5 g bovine serum albumin, pH 6.6.

Next, the labeled anti-T3 and anti-T2, about 10e6 Relative Light Units each, were added in Buffer B containing per liter, 50 mmole sodium phosphate, 150 mmole sodium chloride, 1 mmole EDTA, 0.2 g sodium azide, and 1 g BSA, pH 7.4. After 1 h incubation at about 25 C., the particles were separated magnetically and washed twice with buffer B. The chemiluminescent signals of the two acridinium derivatives were measured using a luminometer equipped with two photmultiplier tubes as described by Law et al. in U.S. Pat. No. 5,395,752, columns 37–42.

A typical calibration curve demonstrating the independence of the binding of anti-T2 on the level of T3 is shown in FIG. 2. This calibration curve was generated using DMAE and LEAE labeled antibodies. We used goat anti-mouse IgG serum diluted 100-fold in the zero calibrator as a model for an interfering factor, and assayed it in the new T3 assay to demonstrated the effect of anti-mouse IgG interference. Addition of this anti-mouse IgG to the T3 calibrator reduced the signal of DMAE-anti-T3 by 60% and concomitantly reduced the signal of LEAE-anti-T2 by 73%. In a real testing situation a 73% decrease LEAE signal would indicate to the assays that that particular sample is abnormal and that the DMAE signal cannot be reliably used for obtaining a accurate T3 concentration. The assayist can then use a sample extraction or other remedial methods and then retest the sample for the real T3 concentration. A more convenient method is, however, given by the use of a correction factor in the present invention. The calibration curves of DMAE and LEAE are run in the absence and in the presence of various concentrations of anti-mouse antibodies and the ratio (or other mathematical relationship) of the two labels in all of these cases is used to correct the DMAE signal and thus obtain the accurate T3 concentration.

Example 2

Non-competitive immunoassay of thyroid stimulating hormone (TSH)

Monoclonal anti-TSH antibodies (7A10 and 11A8) were prepared by immunizations of mice (Balb/c) with human TSH essentially by the methods described in Example 1. An antiidiotypic anti-anti-TSH (11A8) was produced by immunizing mice with Fab2 fragments of anti-TSH (11A8) coupled to maleimide-activated keyhole limphet heamocyanine (Pierce Chemical Co.). The Fab2 fragments was prepared by digestion with pepsin as described in "Antibodies: a laboratory manual" E. D. Harlow and D. Lane Eds. Cold Spring Harbor Pub. 1988, pp. 630-1. Screening for anti-TSH antibodies was done with I-125-TSH and PMP-goat-anti-mouse-IgG. For screening the antiidiotype producing cells, PMP-anti-TSH (7A10) and DMAE-anti-TSH (7A10) were incubated with cell culture supernatants and the presence of antiidiotype was detected by formation of a bridge between the PMP and the label. Inhibition of the bridge formation by TSH was used to confirm the specificity of the antiidioype. Anti-TSH (7A10) was labeled with DMAE, antiidiotype anti-anti-TSH (7A10) was labeled with LEAE, and anti-TSH (11A8) was immobilized on PMP by the same methods as in Example 1.

Figure 4A:
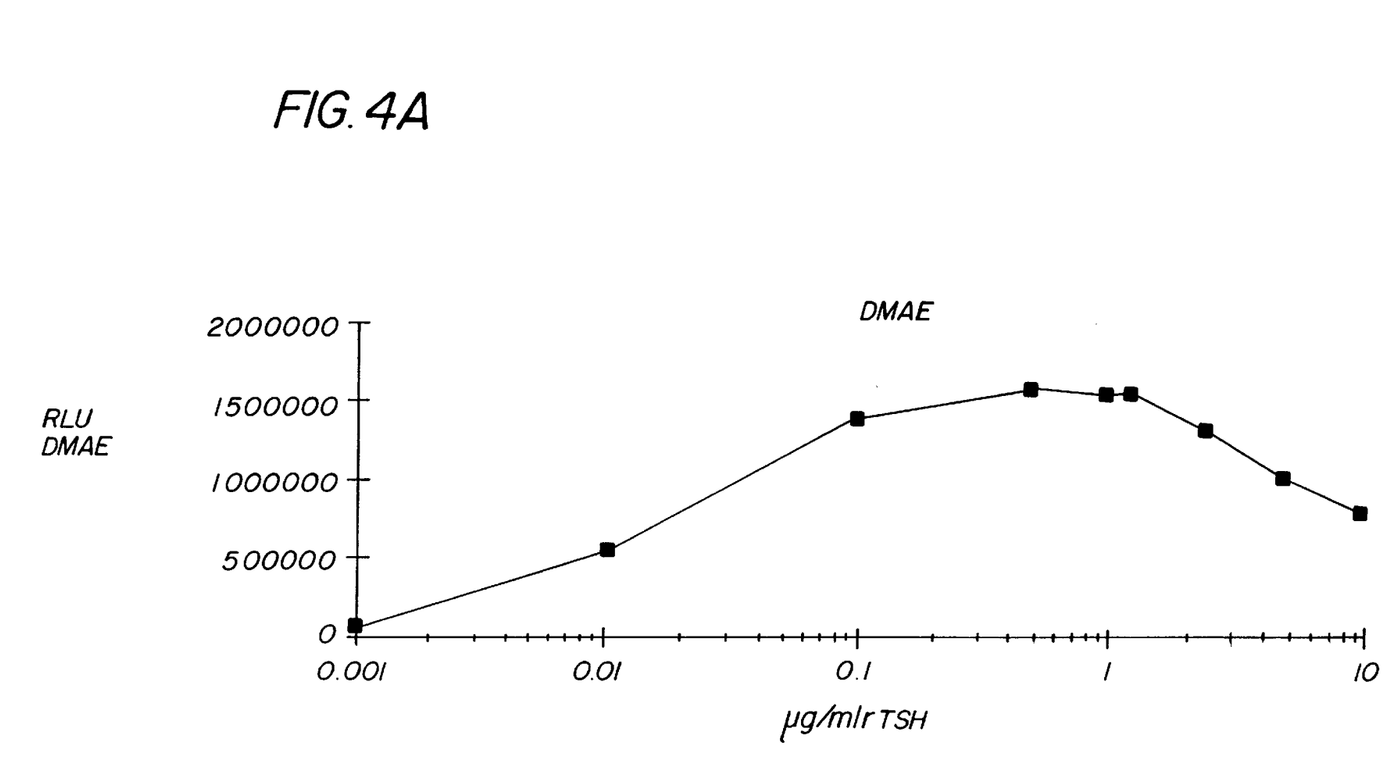
FIG. 4. shows a calibration curves of TSH obtained using DMAE-anti-TSH (top figure) and LEAE-antiidiotype (bottom figure), as described in Example 2.
Figure 4B:
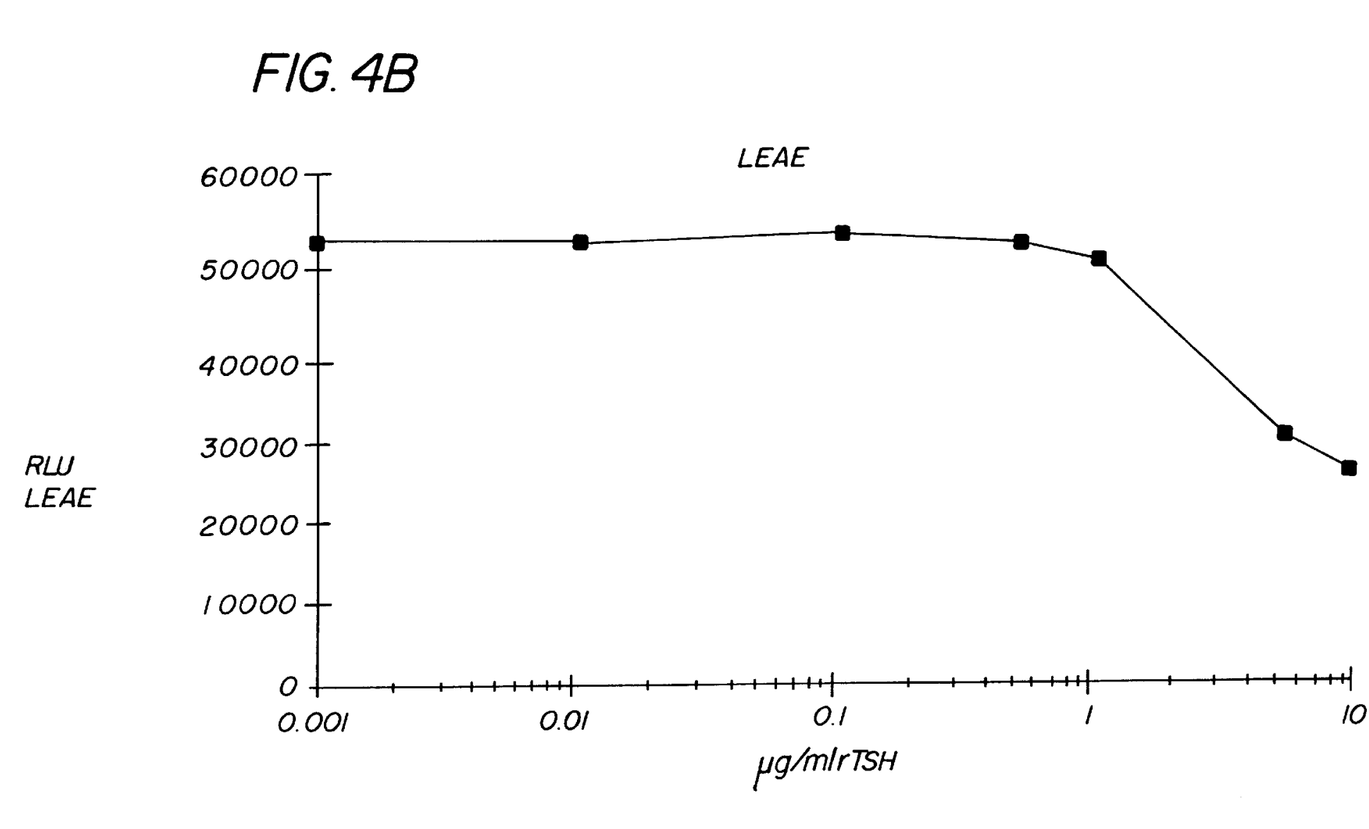

The TSH assay was conducted in polystyrene tubes by mixing 0.1 ml serum calibrator with 0.1 ml mixture of DMAE-anti-TSH(7A10) and LEAE-antiidiotype, 4×10e6 and 2×10e6 RLU, respectively, for 30 min at about 25 C. Next, 50 μg of PMP-anti-TSH(11A8) was added to each tube in 0.5 ml and the incubation was continued for 1 h. Both the solid phase and labeled reagents were added in Buffer B of Example 1. After the incubation the PMP was separated magnetically, washed and counted as in Example 1. The results in FIG. 4 demonstrate the independence of the LEAE-antiidiotype binding to the PMP up to TSH concentration that cause a "high dose hook effect". Thereafter, the decrease in signal is observed with both labeled reagents. In FIG. 3 reaction A represents the case of zero calibrator, reaction B that of low and high calibrators or samples, and reaction D represents the case of a "high dose hook effect." In applying this assay to serum samples, as long as the LEAE signal is about 52,000 RLU the TSH levels determined from the DMAE RLU are deemed valid. If the LEAE RLU are statistically different, the TSH result is "flagged" as invalid. In the absence of other interferences, a readout of LEAE 40,000 RLU and DMAE 130,000 RLU indicates that the correct level of TSH is at 2 μg/ml rather than 0.1 μg/ml. If the sample contains two interfering factors (such as anti-mouse IgG and a high dose hook effect) a third label is used, which is attached to a mouse IgG of irrelevant specificity but with high physical similarity to the labeled anti-TSH. This allowes the assayist to detect the presence of two indepedet interferences, which can then be corrected, each according to its own calibration.

What is claimed is:

1. A binding assay for determining an amount of an analyte in a sample containing interfering factors comprising a. contacting said sample containing said analyte with
(1) a labeled specific binder, labeled with a first label, said labeled specific binder binding to said analyte to form an analyte-labeled specific binder complex,
(2) a solid phase containing an immobilized analyte derivative or mimic, said analyte derivative or mimic binding to said labeled specific binder, and
(3) a labeled reference binder, labeled with a second label, which binds to said analyte derivative or mimic and said interfering factors but which does not bind to said analyte, such that said first label is different from said second label, b. separating said first and second labels which are bound to said solid phase from said unbound labels, c. determining the amount of said first and second labels which are bound to said solid phase, d. comparing the amount of said bound first label with that of reference standards to determine the amount of analyte present , and e. correcting the amount of said analyte present by (1) comparing said amount of said bound second label with that of reference standards to calculate a correction factor, and (2) applying said correction factor to the amount of analyte determined in step d to correct the amount of said analyte.

2. The binding assay of claim 1 in which said analyte is an immunochemical component, genetic material or a receptor.

3. The binding assay of claim 1 in which there are 3 or more labels, each being detectable in the presence of the others, and each being bound to a different analyte or interference in the assay sample.

4. The binding assay of claim 3 in which 2 or more of the labels are affected by different interfering factors.

5. The binding assay of claim 3 in which 2 or more of the labels are affected by different analytes.

6. The binding assay of claim 1 in which said interfering factor increases the signal of said first or second labels.

7. The binding assay of claim 1 in which said interfering factor decreases the signal of said first or second labels.

8. The binding assay of claim 1 in which said labels are chemiluminescent molecules, acridinium esters or derivatives thereof.

9. The binding assay of claim 1 in which said analyte is selected from the group consisting of proteins, peptides, drugs, hormones, receptors, antibodies, microorganisms, environmental pollutants, nucleic acids, lipids, surfactants, carbohydrates, and conjugates of said analytes.

10. The binding assay of claim 1 in which said analyte is selected from the group consisting of whole cells and cell fragments.

11. The binding assay of claim 1 in which said first label is dimethyl acridinium ester, said second label is a long-emission acridinium ester and said solid phase is a paramagnetic particle.

12. The binding assay of claim 1 in which the presence of an interfering factor is qualitatively detected, wherein said step e comprises detecting the presence of said interfering factor by comparing the amount of said second bound label with that of reference standards.

13. A binding assay for determining an amount of an analyte in a sample containing interfering factors comprising a. contacting said sample containing said analyte with
(1) a labeled specific binder, labeled with a first label, said labeled specific binder binding to said analyte to form an analyte-labeled specific binder complex, (2) a solid phase containing an immobilized specific binder, said specific binder binding to said analyte, and (3) a labeled reference binder, labeled with a second label, which binds to said immobilized specific binder and said interfering factors but which does not bind to analyte, such that said first label is different from said second label, b. separating said first and second labels which are bound to said solid phase from said unbound labels, c. determining the amount of said first and second labels which are bound to said solid phase, d. comparing the amount of said bound first label with that of reference standards to determine the amount of analyte present, and e. correcting the amount of said analyte present by (1) comparing said amount of said bound second label with that of reference standards to calculate a correction factor, and (2) applying said correction factor to the amount of analyte determined in step d to correct the amount of said analyte.

14. The binding assay of claim 13 in which said analyte is an antigen, antibody, genetic material or a receptor.

15. The binding assay of claim 13 in which said first label is dimethyl acridinium ester, said second label is a long-emission acridinium ester and said solid phase is a paramagnetic particle.

16. The binding assay of claim 13 in which there are 3 or more labels, each being detectable in the presence of the others, and each being bound to a different analyte or interfering factor in the assay sample.

17. The binding assay of claim 16 in which 2 or more of the labels are bound to different interfering factors.

18. The binding assay of claim 16 in which 2 or more of the labels are bound to different analytes.

19. The binding assay of claim 13 in which the presence of an interfering factor is qualitatively detected, wherein said step e comprises detecting the presence of said interfering factor by comparing the amount of said second bound label with that of reference standards.

20. The binding assay of claim 13 in which said interfering factors increase the signal of said first or second labels.

21. The binding assay of claim 13 in which said interfering factors decrease the signal of said first or second labels.

22. The binding assay of claim 13 in which said labels are chemiluminescent molecules, acridinium esters or derivatives thereof.

23. The binding assay of claim 13 in which said analyte is selected from the group consisting of proteins, peptides, drugs, hormones, receptors, antibodies, microorganisms, environmental pollutants, nucleic acids, lipids, surfactants, carbohydrates, and conjugates of said analytes.

24. The binding assay of claim 13 in which said analyte is selected from the group consisting of whole cells and cell fragments.

* * * * *

UNITED STATES PATENT AND TRADEMARK OFFICE
CERTIFICATE OF CORRECTION

PATENT NO. : 6,087,088
DATED : July 11, 2000
INVENTOR(S) : Uri Piran et al.

It is certified that error appears in the above-identified patent and that said Letters Patent is hereby corrected as shown below:

Column 2,
Line 64, "assays" should read -- assayist --; and

Column 8,
Line 67, "assays" should read -- assayist --.

Signed and Sealed this

Twentieth Day of April, 2004

JON W. DUDAS
*Acting Director of the United States Patent and Trademark Office*